United States Patent
Sakamoto et al.

(10) Patent No.: US 8,846,977 B2
(45) Date of Patent: Sep. 30, 2014

(54) CRYSTALLIZATION UNIT FOR ACRYLIC ACID AND METHOD FOR CRYSTALLIZATION OF ACRYLIC ACID USING THE SAME

(75) Inventors: Kazuhiko Sakamoto, Himeji (JP); Koji Ueno, Himeji (JP); Yoshitake Ishii, Himeji (JP); Masatsugu Kitaura, Himeji (JP)

(73) Assignee: Nippon Shokubai Co. Ltd., Osaka (JP)

( * ) Notice: Subject to any disclaimer, the term of this patent is extended or adjusted under 35 U.S.C. 154(b) by 0 days.

(21) Appl. No.: 13/322,967

(22) PCT Filed: Jun. 24, 2010

(86) PCT No.: PCT/JP2010/060737
§ 371 (c)(1),
(2), (4) Date: Nov. 29, 2011

(87) PCT Pub. No.: WO2011/001887
PCT Pub. Date: Jan. 6, 2011

(65) Prior Publication Data
US 2012/0108857 A1 May 3, 2012

(30) Foreign Application Priority Data
Jun. 30, 2009 (JP) ................. 2009-155605

(51) Int. Cl.
*C07C 51/42* (2006.01)
*C07C 51/43* (2006.01)
*B01D 9/00* (2006.01)

(52) U.S. Cl.
CPC .............. *B01D 9/0013* (2013.01); *C07C 51/43* (2013.01); *B01D 9/0045* (2013.01)
USPC ....................................................... 562/600

(58) Field of Classification Search
CPC combination set(s) only.
See application file for complete search history.

(56) References Cited

U.S. PATENT DOCUMENTS

| | | | |
|---|---|---|---|
| 3,621,664 A | 11/1971 | Saxer | |
| RE32,241 E | 9/1986 | Saxer | |
| 5,935,534 A * | 8/1999 | Umino et al. | ............... 422/245.1 |
| 2004/0216786 A1 | 11/2004 | Yada et al. | |

FOREIGN PATENT DOCUMENTS

| | | |
|---|---|---|
| EP | 0776875 A1 | 6/1997 |
| EP | 1484308 A1 | 12/2004 |
| JP | 53041637 B | 11/1978 |
| JP | 09155101 A | 6/1997 |
| JP | 2003212818 A | 7/2003 |

OTHER PUBLICATIONS

Extended European Search Report from counterpart European Patent Application No. 10794056.1 dated Nov. 27, 2013.

* cited by examiner

*Primary Examiner* — Karl J Puttlitz
(74) *Attorney, Agent, or Firm* — Porzio, Bromberg & Newman, P.C.

(57) ABSTRACT

PROBLEM
An object of the present invention is to provide a crystallization unit capable of producing a purified acrylic acid having high purity efficiently.
SOLUTION
The present invention provides a crystallization unit to separate an acrylic acid-containing solution into a mother liquid and a purified acrylic acid, wherein the crystallization unit comprises a crystallizer having an exit to take out the mother liquid and the purified acrylic acid alternately; a supply line to supply the acrylic acid-containing solution to the crystallizer; and a recovery line to recover the mother liquid and the purified acrylic acid alternately from the crystallizer which is connected to the exit, and wherein the recovery line is equipped with an opening and closing unit consisting of a ball valve or a gate valve.

4 Claims, 1 Drawing Sheet

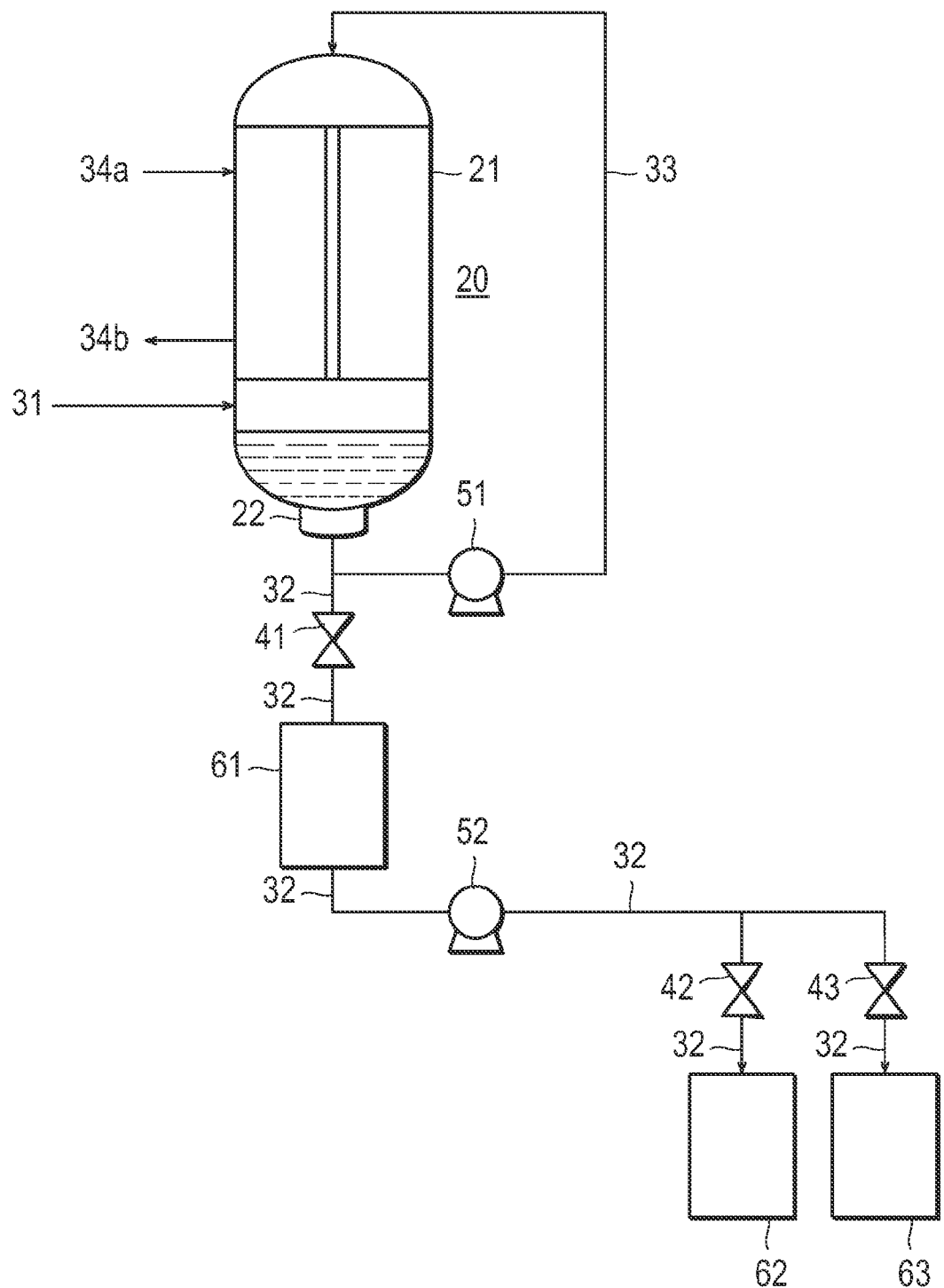

CRYSTALLIZATION UNIT FOR ACRYLIC ACID AND METHOD FOR CRYSTALLIZATION OF ACRYLIC ACID USING THE SAME

CROSS REFERENCE TO RELATED APPLICATION

This is a National Stage of International Application No. PCT/JP2010/060737, filed Jun. 24, 2010, which claims the benefit of Application No. 2009-155605, filed in Japan on Jun. 30, 2009, the disclosures of which Applications are incorporated by reference herein.

TECHNICAL FIELD

The present invention relates to a crystallization unit for acrylic acid and a method for crystallization of acrylic acid using the same. In more detail, the present invention relates to a crystallization unit for acrylic acid which is particularly suitably used in a crystallization step in a process for production of acrylic acid having catalytic gas-phase oxidation step, collection step and/or condensation step, and purification step, and a method for crystallization of acrylic acid using the same.

BACKGROUND ART

An industrial production process of acrylic acid to be widely used currently is mainly composed of (i) catalytic gas-phase oxidation step, (ii) collection step and/or condensation step, and (iii) purification step.

(i) In the catalytic gas-phase oxidation step, acrylic acid is synthesized by catalytic gas-phase oxidation of raw materials of acrylic acid such as propane, propylene and acrolein with a molecular oxygen-containing gas in the presence of an oxidation catalyst. In this case, a mixed gas which contains acrylic acid of desired product and byproducts or impurities (hereinafter, also simply called as "impurities etc.") such as acetic acid, formaldehyde, and acrylic acid dimer is obtained as a reaction product.

(ii) In the collecting step and/or condensation step, the mixed gas containing an acrylic acid and impurities etc. obtained at the above catalytic gas-phase oxidation step is recovered in liquid state. For example, in the collecting step, an acrylic acid-containing solution containing an acrylic acid and impurities etc. is obtained by introducing the above mixed gas into a collecting tower, and collecting the gas by contacting with a collecting solvent such as water.

(iii) In the purification step, a purified acrylic acid in high purity is obtained by purifying the acrylic acid-containing solution obtained at the above collecting step and/or condensation step by a purification means such as distillation step and/or crystallization step. For example, in the crystallization step, firstly acrylic acid is crystallized by cooling the acrylic acid-containing solution, and the mother liquid is recovered. Subsequently, the crystal of acrylic acid is melted to obtain acrylic acid having high purity. It should be noted that, the term "mother liquid" as used herein means a solution that remains after depositing the crystal of acrylic acid from the acrylic acid-containing solution.

A crystallization unit to be used in such crystallization step generally has a crystallizer, a supply means to supply the acrylic acid-containing solution into the crystallizer, and a recovery means to recover the mother liquid or the purified acrylic acid.

For example, Patent Literature 1 discloses a crystallization method using a multistage fractional crystallization method. And, as a crystallization unit to be used for the method, a crystallization unit having piping equipped with valves therein to transport melted liquid of the crystal and the mother liquid obtained at the crystallization unit into a tank has been disclosed.

In addition, Patent Literature 2 discloses a crystallization method in which, when crystal is melted, a polymerization inhibitor is added to a heated purified melted liquid, and this solution is circulated and supplied to crystal to melt the crystal, and both melted liquid from crystal and purified melted liquid are recovered. Also, a unit has been disclosed in which the melted liquid from crystal and the mother liquid from the crystallization unit are transported to tanks through piping equipped with valves therein, when the melted liquid from crystal and the melted purified liquid containing a polymerization inhibitor added thereto are recovered.

PRIOR ART LITERATURE

Patent Literature

Patent Literature 1: JP-B-53-041637
Patent Literature 2: JP-A-09-155101

DISCLOSURE OF THE INVENTION

Problem to be Solved by the Invention

However, there was a problem that when acrylic acid was purified using the unit described in the above Patent Literatures 1 and 2, the mother liquid, which was remaining inside of the transportation controlling units such as valves and pumps equipped in the recovery line or on the way of the recovery line as a stagnant liquid, is mixed into the purified acrylic acid in recovery of the purified acrylic acid from the crystallizer, and the purified acrylic acid having desired purity could not be obtained. It is current situation that improvement in purity is always desired because an impurity etc. of even a ppm level could accelerate or inhibit polymerization of acrylic acid.

Thus, it is an object of the present invention to provide a crystallization unit which is capable of producing a purified acrylic acid having high purity efficiently.

Means for Solving the Problem

The present inventors have intensively studied to solve the above problem. As a result, the present inventors have found that a purified acrylic acid having high purity can be efficiently obtained by using a ball valve or a gate valve as an opening and closing unit to be equipped in the recovery line to recover alternately the mother liquid and the purified acrylic acid from the crystallizer, and completed the present invention.

That is, the present invention is a crystallization unit to separate an acrylic acid-containing solution into a mother liquid and a purified acrylic acid, wherein the crystallization unit has a crystallizer having an exit to take out the mother liquid and the purified acrylic acid alternately; a supply line to supply the acrylic acid-containing solution to the crystallizer; and a recovery line which is connected to the exit and recovers the mother liquid and the purified acrylic acid alternately from the crystallizer; and the recovery line is equipped with an opening and closing unit consisting of a ball valve or a gate valve.

In addition, the present invention provides a method for crystallization of the acrylic acid by performing the following steps (A) to (D) using the above crystallization unit: (A) crystallization step in which acrylic acid is crystallized by cooling the acrylic acid-containing solution supplied through the supply line in the crystallizer; (B) mother liquid recovery step in which the mother liquid obtained at the crystallization step is recovered from the recovery line by opening the opening and closing unit in the recovery line; (C) melting step in which after closing the opening and closing unit in the recovery line, acrylic acid is melted by heating the crystal of acrylic acid obtained at the crystallization step; and (D) purified acrylic acid recovery step in which the purified acrylic acid obtained at the melting step is recovered from the recovery line by opening the opening and closing unit in the recovery line.

Effect of the Invention

According to the crystallization unit of the present invention, acrylic acid having high purity can be efficiently obtained.

BRIEF DESCRIPTION OF THE DRAWING

[FIG. 1]
FIG. 1 is a schematic diagram diagrammatically representing a batch type dynamic crystallization unit according to one embodiment of the present invention.

ASPECTS FOR CARRYING OUT THE INVENTION

Hereinafter, embodiments of the present invention will be described by reference to the accompanying drawing. It should be noted that, in the description of the drawing, the same elements have the same symbols and repeated explanations have been omitted. In addition, dimension and ratio of the drawing have been emphasized for convenience of explanation, and may be different from actual ratio.
<Crystallization Unit>
FIG. 1 is a schematic diagram diagrammatically representing a batch type dynamic crystallization unit according to one embodiment of the present invention. According to FIG. 1, the crystallization unit 10 mainly has crystallizer 20, various lines connected to crystallizer 20, and various tanks to store the mother liquid or the purified acrylic acid.

Crystallizer 20 has a crystallization tube 21 therein. On the inner wall side of crystallization tube 21, the acrylic acid-containing solution is circulating, and when crystallization tube 21 is cooled, crystal of acrylic acid grows up on the inner wall side of crystallization tube 21. On the outer wall side of crystallization tube 21, channels in which a medium to cool down or heat up crystallization tube 21 flows are installed. In an industrial large scale production, around 1,000 to 2,000 of crystallization tubes 21 per one crystallizer 20 are usually installed, but only one tube is illustrated for simplification in FIG. 1. Further, in the bottom of crystallizer 20, exit 22 to take out the mother liquid and the purified acrylic acid alternately is installed.

In crystallizer 20, supply line 31 to supply the acrylic acid-containing solution obtained at the collecting step and/or the condensation step and recovery line 32 connected to exit 22 and to recover the mother liquid and the purified acrylic acid are installed. Further, circulation line 33 to transport the acrylic acid-containing solution accumulated in the tower bottom section to the tower top section and medium line (34a, 34b) to supply or recover the medium are connected to crystallizer 20.

In the various lines described above, in order to control flow of each liquid, ball valves (41, 42, 43) and pumps (51, 52) are installed.

Furthermore, on the way of or on the end of recovery line 32, tanks to store the mother liquid or the purified acrylic acid obtained by the crystallization are installed. In FIG. 1, recovery tank 61 on the way of recovery line 32, mother liquid tank 62 to store the mother liquid on the end of recovery line 32, and purified acrylic acid tank 63 to store the purified acrylic acid are installed.

Hereinafter, each constituent element of the crystallization unit of the present aspect will be explained.
[Crystallizer]
The crystallizer of the present aspect is a batch type crystallizer, in which the acrylic acid-containing solution is separated into mother liquid and acrylic acid having high purity by crystallizing acrylic acid contained in the acrylic acid-containing solution followed by melting. As the crystallizer, any conventional well known one may be employed accordingly, and type or size thereof is not particularly limited. Crystallization in the crystallizer is roughly classified into dynamic crystallization in which crystallization is carried out while the acrylic acid-containing solution is flowing and static crystallization in which crystallization is carried out while the acrylic acid-containing solution is not flowing. Any crystallizer employing either method of crystallization may be used. Specific example of the crystallizer includes layered crystallization unit (dynamic crystallization unit) manufactured by Sulzer Chemtech, static crystallization unit manufactured by BEFS PROKEM, and the like.

When crystallizer is the layered crystallization unit, the crystallizer is usually installed with around 1,000 to 2,000 of crystallization tubes to grow up crystal. And, on the outer wall side of the crystallization tubes, channels in which a medium to cool down or heat up the crystallization tubes flows are arranged.

In addition, in the tower bottom section of the crystallizer, an exit to take out the mother liquid and the purified acrylic acid alternately is installed.
[Supply Line]
In the crystallizer, a supply line to supply the acrylic acid-containing solution obtained via catalytic gas-phase oxidation step and collection step and/or condensation step is installed. Installation location of the supply line is not particularly limited, but in order to transport the acrylic acid-containing solution to upper part of the crystallization tube by circulation pump 51, the supply line is preferably installed in the vicinity of the tower bottom section like supply line 31 in FIG. 1.
[Recovery Line]
A recovery line to recover the mother liquid and the purified acrylic acid alternately is connected to the exit of the crystallizer. On the way of the recovery line, recovery tank 61 to recover the mother liquid and the purified acrylic acid can be installed as in FIG. 1. In addition, the end of the recovery line may be connected to mother liquid tank 62 to store the mother liquid or purified acrylic acid tank 63 to store the purified acrylic acid as in FIG. 1, or may be directly connected to a purifying apparatus such as crystallizer or distillation tower for further purification.

The recovery line may be implemented by a single system of common recovery line for recovering the mother liquid and the purified acrylic acid as in FIG. 1, or by multiple systems of recovery lines to recover the mother liquid and the purified acrylic acid separately. However, from the viewpoint of reducing the stagnant liquid remaining on inner wall of the recovery line and inside of the opening and closing units, the recovery line desirably has a configuration as short as and as simple as possible, and hence a single system of recovery line is more preferable.

Transportation of the mother liquid and the purified acrylic acid in the recovery lines from the crystallizer to various kinds of tanks (61, 62, 63) may be by free fall or by using pump installed in the recovery line as a power source, but transportation by free fall is preferable because of less stagnant liquid (the mother liquid or the purified acrylic acid remaining in the recovery line).

[Opening and Closing Unit]

In the recovery line, ball valves or gate valves are installed as opening and closing units to control transportation of the mother liquid or the purified acrylic acid.

The ball valve is an ON-OFF valve in which a valve body has ball-shaped (ball) and opening and closing is performed by turning a handle (valve axis) by 90 degree. The valve body of the ball valve includes perfect ball type, segment type, and the like, and perfect ball type is preferable because it has less resistance in liquid passing and capable of reducing stagnant liquid occurring in closed time by reducing size thereof. Type of bore diameter of the valve includes full-bore type, reduced-bore type, and the like, but full-bore type is preferable because loss in flow rate hardly occurs. In addition, structure of the valve includes floating type and trunnion type, but any type may be used.

On the other hand, the gate valve is also called as partition valve, and opening and closing is performed by a disk-like valve body stored in a valve box of the valve moving vertically against flow channel. These ball valve and gate valve have less resistance in liquid passing due to their simple structures, and also capable of reducing the stagnant liquid in closed time by making smaller size than other type of valve.

Both these ball valve and gate valve are difficult to prevent liquid passing of the mother liquid or the purified acrylic acid in the recovery line due to their low fluid resistances. Thus, even when it is required to ensure a desired flow rate, a smaller sized valve compared with that of other types can be installed to minimize stagnant liquid in the valve. Among the ball valve and the gate valve, the ball valve is preferable from the viewpoint of easy adjustment of valve opening.

Installment location of the ball valve or the gate valve in the recovery line is not particularly limited. In this regard, however, from the viewpoint of reducing stagnant liquid much more, the valve should be equipped preferably in the recovery line section in which the mother liquid and the purified acrylic acid flow by free fall, and more preferably in the recovery line section which extends in the vertical direction. In addition, in the recovery line, at least one ball valve or gate valve may be installed, and any valve other than these types may be used if necessary. However, in order to make the effect of the present invention more significant, preferably majority of the valves installed is the ball valve or the gate valve. Thus, the most preferable aspect is the one in which all of valves to be installed in the recovery line are either the ball valve or the gate valve.

As in the case of crystallization unit of the present aspect, even the unit in which the mother liquid and the purified acrylic acid are recovered through a common recovery line alternately, mixing of the mother liquid into the purified acrylic acid can be prevented effectively and the purified acrylic acid having higher purity can be obtained by using the above valve which has less stagnant liquid. In addition, these valves can avoid decrease of flow rate due to their low fluid resistances. Thus, a series of crystallization steps can be completed within a shorter time.

In the crystallization unit of the present aspect, besides the above parts, a circulation line to circulate the tower bottom liquid of the crystallizer to the tower top section and a medium line to supply medium to the crystallizer or recover medium from the crystallizer are installed. It should be noted that, temperature of the medium can be adjusted by the heating and cooling unit of the medium to be connected to the medium line.

<Crystallization Method>

Next, the crystallization method for acrylic acid using the above crystallization unit will be explained.

The crystallization method for acrylic acid of the present aspect includes the following steps (A) to (D): (A) crystallization step in which acrylic acid is crystallized by cooling the acrylic acid-containing solution supplied through the supply line in the crystallizer; (B) mother liquid recovery step in which the mother liquid obtained at the crystallization step is recovered from the recovery line by opening the opening and closing unit in the recovery line; (C) melting step in which after closing the opening and closing unit in the recovery line, acrylic acid is melted by heating up the crystal of acrylic acid obtained at the crystallization step; and (D) purified acrylic acid recovery step in which the purified acrylic acid obtained at the melting step is recovered from the recovery line by opening the opening and closing unit in the recovery line.

And, the above crystallization method may further include the following step (X) after the crystallization step (A) and before the melting step (C) if necessary: (X) sweating step in which impurities contained in the crystal is removed by heating the crystal of acrylic acid in the crystallizer.

Hereinafter, each step of the crystallization method of the present aspect will be explained citing the case where the crystallization unit of FIG. 1 is used.

(A) Crystallization Step

In the crystallization step, acrylic acid is crystallized by cooling the acrylic acid-containing solution supplied through the supply line. Crystallization method for acrylic acid is not particularly limited, and either the dynamic crystallization or the static crystallization may be used, however, the dynamic crystallization is preferably used. It is because the dynamic crystallization has an advantage that mixing of the mother liquid into crystal is less.

In the case where the crystallization unit of FIG. 1 is used, the acrylic acid-containing solution supplied to crystallizer 20 accumulates in the tower bottom section, and the solution is circulated to the tower top section through circulation line 33. By this circulation, the acrylic acid-containing solution flows down like falling film along the surface of the inner wall of crystallization tube 21. And, crystallization tube 21 is cooled from outside of the tube by supplying a cooling medium from medium line (34a, 34b). In this instance, temperature of the cooling medium is adjusted so that temperature of the surface of inner wall of crystallization tube 21 falls within the desired range. As crystallization tube 21 is cooled, acrylic acid contained in the acrylic acid-containing solution crystallizes on the surface of the inner wall, and the crystal further grows up. After around 60 to 90% by mass of acrylic acid contained in the acrylic acid-containing solution is crystallized, the circulation of the acrylic acid-containing solution is stopped by turning off pump 51.

(B) Mother Liquid Recovery Step

In the mother liquid recovery step, the mother liquid accumulated in the tower bottom section in the above crystallization step is transported to recovery tank 61 through recovery line 32 by opening a ball valve 41 installed in recovery line 32 for the mother liquid. Subsequently, the mother liquid stored in recovery tank 61 is recovered into mother liquid tank 62 through recovery line 32 by closing a ball valve 41, opening a ball valve 42, and actuating pump 52. The mother liquid contains, besides acrylic acid remaining without being crystallized, impurities etc. in high concentrations. Acrylic acid contained in this mother liquid can be separated through a purification step such as distillation and crystallization again.
(C) Melting Step In the melting step, the crystal of acrylic acid obtained at the above crystallization step is melted. Firstly, ball valves (41, 42) installed in recovery line 32 for the mother liquid are closed. Subsequently, heating medium is supplied through medium line (34a, 34b) to heat up crystallization tube 21. As temperature of crystallization tube 21 goes up, the crystal of acrylic acid adhered on the inner wall of crystallization tube 21 is melted, and melted liquid from the crystal of acrylic acid is accumulated in the tower bottom section. In this instance, temperature of the inner wall of crystallization tube 21 is preferably around 20 to 40° C. In addition, the melted liquid accumulated in the tower bottom section is preferably circulated to the tower top section through circulation line 33 to flow down along the surface of the crystal of acrylic acid which is remaining without melting yet. By this circulation, melting of the crystal is accelerated.

In the melting, preferably a polymerization inhibitor is added to the melted liquid of the crystal of acrylic acid. The polymerization inhibitor is not particularly limited, and includes, for example, N-oxyl compound such as 2,2,6,6-tetramethylpiperidino-1-oxyl; phenol compound such as p-methoxyphenol; manganese salt compound such as manganese acetate; copper salt compound of dialkyldithiocarbamic acid such as copper dibutyldithiocarbamate; nitroso compound; amine compound; and phenothiazine compound; and the like. Among them, preferably at least one kind of compound selected from the group consisting of N-oxyl compound such as 2,2,6,6-tetramethylpiperidino-1-oxyl; phenol compound such as p-methoxyphenol; and manganese salt compound such as manganese acetate is used. By using these polymerization inhibitor, acrylic acid having more excellent color tone and sufficiently high quality can be obtained.

The polymerization inhibitor may be added to the melted liquid as it is, or a solution of the polymerization inhibitor is prepared separately, and the solution may be added to the melted liquid. When the solution of the polymerization inhibitor is prepared, acrylic acid, water, acetic acid, or the like can be used as a solvent, but acrylic acid is preferably used. In addition, the addition site where the polymerization inhibitor or the polymerization inhibitor solution is added is not particularly limited, and they may be added directly to the tower bottom liquid or may be added through an adding device which is provided in line 33 separately during circulation of the tower bottom liquid through line 33.
(D) Purified Acrylic Acid Recovery Step In the purified acrylic acid recovery step, the purified acrylic acid obtained at the above melting step (C) is transported to recovery tank 61 through recovery line 32 by opening a ball valve 41. Subsequently, the purified acrylic acid stored in recovery tank 61 is recovered to purified acrylic acid tank 63 through recovery line 32 by closing a ball valve 41, opening a ball valve 43, and actuating a pump 52. The recovered solution of the purified acrylic acid can be purified through further distillation, crystallization, or the like, if necessary.

(X) Sweating Step

In the sweating step, by heating up the crystal of acrylic acid obtained at the above crystallization step, impurities contained in the crystal are removed. Firstly, the supply through medium line (34a, 34b) is changed from cooling medium to the heating medium to heat up crystallization tube 21. In this instance, temperature of the heating medium is controlled so that temperature of the inner wall of crystallization tube 21 becomes higher than the freezing point of crystal by 0 to 5° C. By keeping the crystal under this condition and melting a part (around 1 to 10% by mass) of the crystal, the impurities etc. taken in the crystal are released outside and purity of the crystal is increased.

The sweating liquid accumulated in the tower bottom section in the above sweating step is recovered to recovery tank 61 through recovery line 32 for the mother liquid by opening a ball valve 41. The sweating liquid stored in recovery tank 61 is recovered to mother liquid tank 62 through recovery line 32 by closing a ball valve 41, opening a ball valve 42, and actuating a pump 52. Acrylic acid contained in the recovered sweating liquid is separated through a purification step such as distillation, crystallization again together with the mother liquid and the like.

The sweating step can be carried out after the above crystallization step (A) and before the melting step (C). As in Example described later, by performing the sweating step (X) after the above crystallization step (A) and before the mother liquid recovery step (B), the sweating liquid generated in the sweating step can be recovered in the mother liquid recovery step (B) together with the mother liquid. Alternatively, the sweating step (X) and a recovery step to recover an impurities-containing liquid generated in the step may be provided separately after the mother liquid recovery step (B) and before the melting step (C).

Since the crystallization method of the present aspect uses the crystallization unit in which ball valve or gate valve is installed in the recovery line to recover the mother liquid and the purified acrylic acid alternately, acrylic acid having higher purity can be obtained efficiently compared with the case where a conventional crystallization unit is used.

EXAMPLES

Effect of the present invention will be explained using the following Example and Comparative Examples. In this regard, however, the technical scope of the present invention is not limited only to the following Example.

Example 1

A mixed gas obtained by a catalytic gas-phase oxidation reaction of propylene was introduced to the collection tower, and contacted with an aqueous solution for collection to obtain an acrylic acid-containing solution at a rate of 6.65 kg/hour. Composition of the acrylic acid-containing solution was as shown in Table 1. It should be noted that, the catalytic gas-phase oxidation reaction was carried out in the same manner as in Example 1 of JP-A-2005-15478 (US-A-2004-249199). In addition, temperature of the tower bottom liquid (that is, acrylic acid-containing solution) of the collection tower was 91° C.
(First Crystallization Operation)
(A) Crystallization Step Next, after cooling the above acrylic acid-containing solution, the solution was introduced into crystallizer 20 through supply line 34 of crystallization unit 10 shown in FIG. 1. And, by actuating a pump 51, the acrylic acid-containing solution was flown down like falling film along the surface of inner wall of crystallization tube 21. Temperature of the inner wall of crystallization tube 21 was decreased to the freezing point of acrylic acid or lower by supplying a cooling medium through medium line 34a, to crystallize a part (about 60 to 90% by mass in each of the first to the fourth crystallization operations) of acrylic acid contained in the acrylic acid-containing solution on the surface of inner wall.

(X) Sweating Step and (B) Mother Liquid Recovery Step

Temperature of the inner wall of crystallization tube 21 was raised up to around the freezing point by turning off a pump 51 to develop sweating of the crystal and remove impurities contained in the crystal. About 2 to 5% by mass of the crystal of acrylic acid in each of the first to the fourth sweating were melted. Mixed liquid of the mother liquid obtained at the above crystallization step and the sweating liquid generated by the sweating was transported from exit 22 in the tower bottom section to recovery tank 61 through the recovery line by opening a ball valve 41. And, the mother liquid stored in recovery tank 61 was recovered to mother liquid tank 62 through recovery line 32 by closing a ball valve 41, opening a ball valve 42, and actuating a pump 52.

(C) Melting Step and (D) Purified Acrylic Acid Recovery Step

The crystal was melted by supplying a heating medium at 37° C. to the crystallizer. And, the melted liquid accumulated in the tower bottom section was circulated to the tower top section through circulation line 33 to flow down along the surface of the crystal of acrylic acid. After completion of the melting, the resultant purified acrylic acid (first time) was transported from exit 22 of the tower bottom section to recovery tank 61 through the recovery line by opening a ball valve 41. Subsequently, the purified acrylic acid (first time) stored in recovery tank 61 was transported to purified acrylic acid tank 63 through recovery line 32 by closing a ball valve 41, opening a ball valve 43, and actuating pump 52.

(Second Crystallization Operation)

The second crystallization operation was carried out in the same manner as in the first crystallization operation except that the purified acrylic acid (first time) stored in purified acrylic acid tank 63 in the first crystallization operation was used as the acrylic acid-containing solution, to obtain the purified acrylic acid (second time).

(Third Crystallization Operation)

The third crystallization operation was carried out in the same manner as in the first crystallization operation except that the purified acrylic acid (second time) stored in purified acrylic acid tank 63 in the second crystallization operation was used as the acrylic acid-containing solution, and that in the melting step, an acrylic acid solution containing 5% by mass of p-methoxyphenol was added before starting the melting (before raising temperature of crystallization tube 21), to obtain the purified acrylic acid (third time).

(Fourth Crystallization Operation)

The fourth crystallization operation was carried out in the same manner as in the third crystallization operation except that the purified acrylic acid (third time) stored in purified acrylic acid tank 63 in the third crystallization operation was used as the acrylic acid-containing solution, to obtain the purified acrylic acid (fourth time) at a rate of 3.32 kg/hour. Composition of the purified acrylic acid (forth time) stored in purified acrylic acid tank 63 after completion of the fourth crystallization operation was as shown in the following Table 1.

Comparative Example 1

A crystallization operation was carried out in the same manner as in Example 1 except that the ball valves (41, 42, 43) of the crystallization unit in FIG. 1 were replaced with butterfly valves each having the same diameter to those of the ball valves in Example 1, to obtain the purified acrylic acid at a rate of 2.86 kg/hour.

Comparative Example 2

A crystallization operation was carried out in the same manner as in Example 1 except that the ball valves (41, 42, 43) of the crystallization unit in FIG. 1 were replaced with butterfly valves each having a diameter 2 times larger than those of the ball valves in Example 1, to obtain the purified acrylic acid at a rate of 3.31 kg/hour.

TABLE 1

| | Acrylic acid-containing solution | Purified acrylic acid (fourth time) | | |
|---|---|---|---|---|
| | | Example 1 | Comparative Example 1 | Comparative Example 2 |
| Acrylic acid | 90.0% | 99.94% | 99.93% | 99.90% |
| Water | 3.2% | 92 ppm | 95 ppm | 120 ppm |
| Acetic acid | 1.9% | 450 ppm | 470 ppm | 520 ppm |
| Maleic acid | 0.6% | 2 ppm | 2 ppm | 3 ppm |
| Acrylic acid dimer | 1.5% | 41 ppm | 58 ppm | 110 ppm |
| Furfural | 0.07% | 0.2 ppm | 0.2 ppm | 0.3 ppm |
| Benzaldehyde | 0.27% | 0.1 ppm | 0.1 ppm | 0.2 ppm |
| Formaldehyde | 0.06% | 0 ppm | 0 ppm | 0 ppm |
| Hydroquinone | 0.1% | — | — | — |
| Other impurities | 2.3% | — | — | — |

In the above Table, "%" means "% by mass" and "ppm" means "ppm by mass".

From the above results, it was shown that acrylic acid having higher purity could be obtained in Example 1 compared with that in Comparative Example 1. In addition, production amount of the purified acrylic acid per hour in Example 1 was equal to that in Comparative Example 2.

It should be noted that, the present application is based on Japanese Patent Application No. 2009-155605, filed on Jun. 30, 2009, and the disclosed content of which is hereby incorporated by reference in its entirety into this application.

[Description of Symbol]
- 10: Crystallization unit
- 20: Crystallizer
- 21: Crystallization tube
- 22: Exit
- 31: Supply line
- 32: Recovery line
- 33: Circulation line
- 34a, 34b: Medium line
- 41, 42, 43: Ball valve
- 51, 52: Pump
- 61: Recovery tank
- 62: Mother liquid tank
- 63: Purified acrylic acid tank

The invention claimed is:

1. A method for crystallization of acrylic acid comprising the following steps:
   (A) supplying an acrylic acid-containing solution through a supply line to a crystallizer;
   (B) cooling the acrylic acid-containing solution in the crystallizer for crystallization to separate said acrylic acid-containing solution into a mother liquid and crystals of purified acrylic acid;
   (C) recovering the mother liquid in a recovery line at an exit of said crystallizer by opening said recovery line using a ball valve;

(D) melting said crystals of purified acrylic acid in said crystallizer after closing of said ball valve by heating said crystals of purified acrylic acid; and (E) recovering purified acrylic acid obtained at step (D) from said recovery line by opening said recovery line with said ball valve.

2. The method for crystallization of acrylic acid according to claim 1, further comprising the following step (X):

(X) a sweating step in which impurities contained in said crystals of purified acrylic acid and removed by heating said crystals of acrylic acid in said crystallizer;

after step (A) and prior to step (D).

3. The method for crystallization of acrylic acid according to claim 2, wherein the mother liquid further comprises the sweating liquid obtained by said sweating step (X) carried out following step (A).

4. The method for crystallization of acrylic acid according to claim 1, wherein the crystallization is a dynamic crystallization.

* * * * *